(12) United States Patent
Podmore

(10) Patent No.: US 9,387,119 B2
(45) Date of Patent: *Jul. 12, 2016

(54) ORAL DEVICE FOR ANTERIOR ADVANCEMENT OF THE TONGUE

(71) Applicant: ApniCure, Inc., Redwood City, CA (US)

(72) Inventor: Jonathan L. Podmore, San Carlos, CA (US)

(73) Assignee: ApniCure, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,045

(22) Filed: Jul. 16, 2013

(65) Prior Publication Data

US 2014/0053851 A1    Feb. 27, 2014

Related U.S. Application Data

(63) Continuation-in-part of application No. 13/759,793, filed on Feb. 5, 2013, which is a continuation of application No. 13/593,137, filed on Aug. 23, 2012, now Pat. No. 8,387,620.

(51) Int. Cl.
*A61F 5/56* (2006.01)

(52) U.S. Cl.
CPC .................................... *A61F 5/566* (2013.01)

(58) Field of Classification Search
USPC ............. 128/848, 859–862; 433/6–7; 602/902
See application file for complete search history.

(56) References Cited

U.S. PATENT DOCUMENTS

| | | | |
|---|---|---|---|
| 5,720,302 A * | 2/1998 | Belfer | A61F 5/566 128/848 |
| 5,876,199 A | 3/1999 | Bergersen | |
| 5,957,133 A * | 9/1999 | Hart | A61F 5/566 128/200.26 |
| 6,467,484 B1 | 10/2002 | De Voss | |
| 6,494,209 B2 * | 12/2002 | Kulick | A61F 5/566 128/848 |
| 6,595,209 B1 | 7/2003 | Rose et al. | |
| 6,997,177 B2 | 2/2006 | Wood | |
| 7,328,698 B2 * | 2/2008 | Scarberry et al. | 128/200.24 |
| 7,954,494 B1 | 6/2011 | Connor | |
| 8,074,656 B2 | 12/2011 | Vaska et al. | |
| 8,122,889 B2 | 2/2012 | Vaska et al. | |
| 8,122,890 B2 | 2/2012 | Vaska | |
| 8,387,620 B1 | 3/2013 | Vaska et al. | |

(Continued)

OTHER PUBLICATIONS

U.S. Appl. No. 13/476,855, filed May 21, 2012, Podmore et al.
U.S. Appl. No. 13/546,453, filed Jul. 11, 2012, Vitale et al.
U.S. Appl. No. 13/759,793, filed Feb. 5, 2013, Vaska et al.
Office action dated Oct. 18, 2012 for U.S. Appl. No. 13/593,137.
Tsuiki, et al. Tongue position controller as an alternative treatment for obstructive sleep apnea. American Journal of Respiratory and Critical Care Medicine 2012; 185:A6461.

(Continued)

*Primary Examiner* — Ophelia A Hawthorne
(74) *Attorney, Agent, or Firm* — Wilson, Sonsini, Goodrich & Rosati

(57) ABSTRACT

An oral device for temporary placement in a patient's oral cavity includes a base and a tongue pocket. Partial vacuums are separately drawn through vertically oriented, tooth facing ports on the base and the tongue pocket in order to advance and control the position of the tongue in order to clear the patient's airway to reduce sleep apnea or treat other conditions.

46 Claims, 10 Drawing Sheets

(56) References Cited

U.S. PATENT DOCUMENTS

| | | |
|---|---|---|
| 2005/0166928 A1* | 8/2005 | Jiang ................ A61F 5/566 128/861 |
| 2005/0166929 A1 | 8/2005 | Jiang |
| 2007/0277818 A1 | 12/2007 | Chen |
| 2009/0120446 A1 | 5/2009 | Vaska et al. |
| 2009/0120447 A1 | 5/2009 | Vaska et al. |
| 2009/0123886 A1 | 5/2009 | Vaska |
| 2009/0188510 A1 | 7/2009 | Palmer |
| 2011/0220124 A1 | 9/2011 | Vaska et al. |
| 2011/0259346 A1 | 10/2011 | Tsuiki et al. |
| 2012/0017917 A1 | 1/2012 | Podmore et al. |
| 2012/0037166 A1 | 2/2012 | Podmore et al. |
| 2012/0132215 A1 | 5/2012 | Vaska et al. |
| 2012/0132216 A1 | 5/2012 | Vaska |
| 2012/0199135 A1 | 8/2012 | Podmore et al. |
| 2012/0199137 A1 | 8/2012 | Zacharopoulos |
| 2014/0053849 A1 | 2/2014 | Vaska et al. |

OTHER PUBLICATIONS

International search report and written opinion dated Nov. 12, 2013 for PCT/US2013/055734.

Lazard, et al. The tongue-retaining device: efficacy and side effects in obstructive sleep apnea syndrome. J Clin Sleep Med. Oct. 15, 2009;5(5):431-8.

Office action dated Jun. 20, 2014 for U.S. Appl. No. 13/759,793.

Office action dated Dec. 22, 2014 for U.S. Appl. No. 13/759,793.

Office action dated Jun. 16, 2015 for U.S. Appl. No. 13/759,793.

* cited by examiner

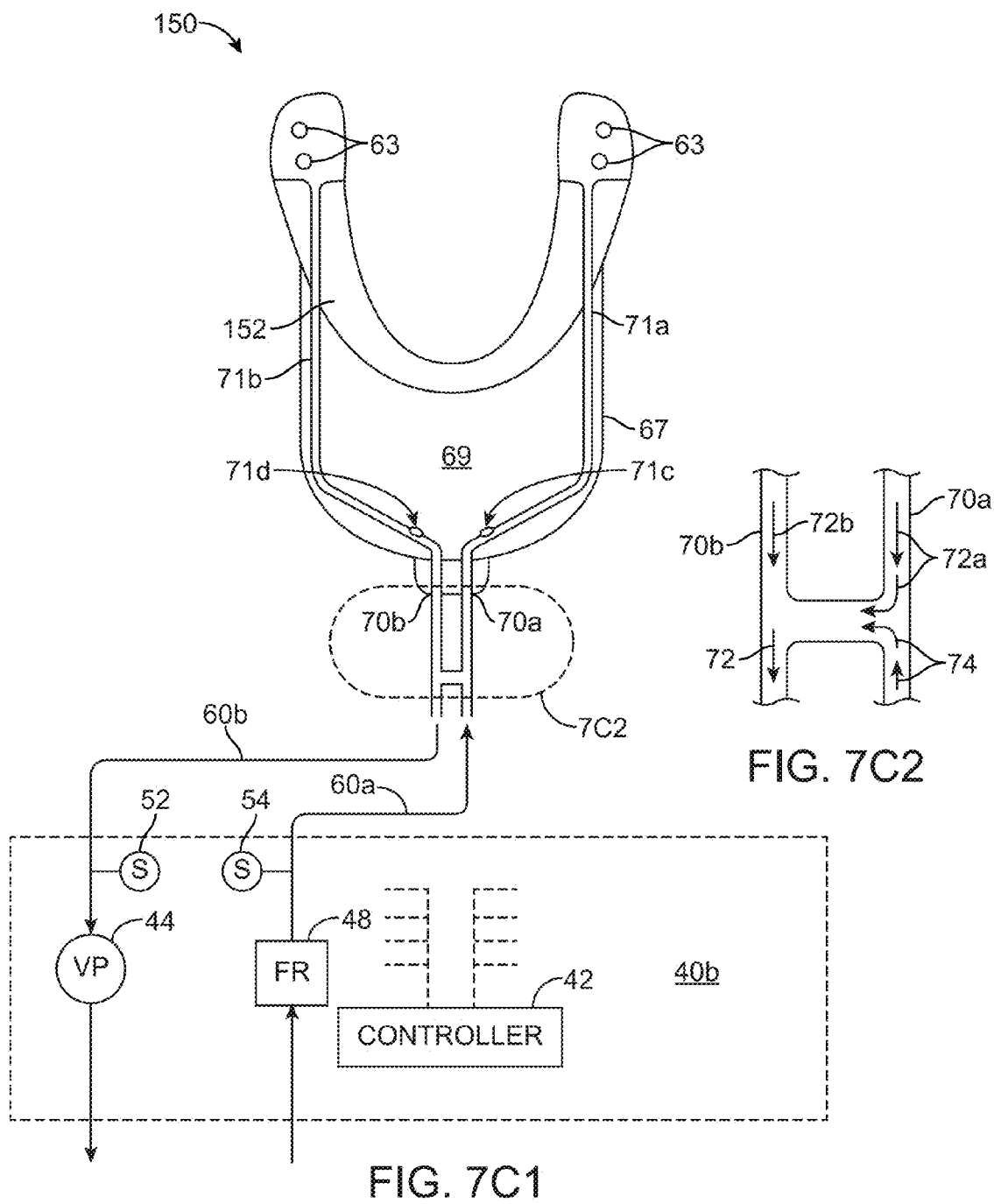
FIG. 7C1
FIG. 7C2

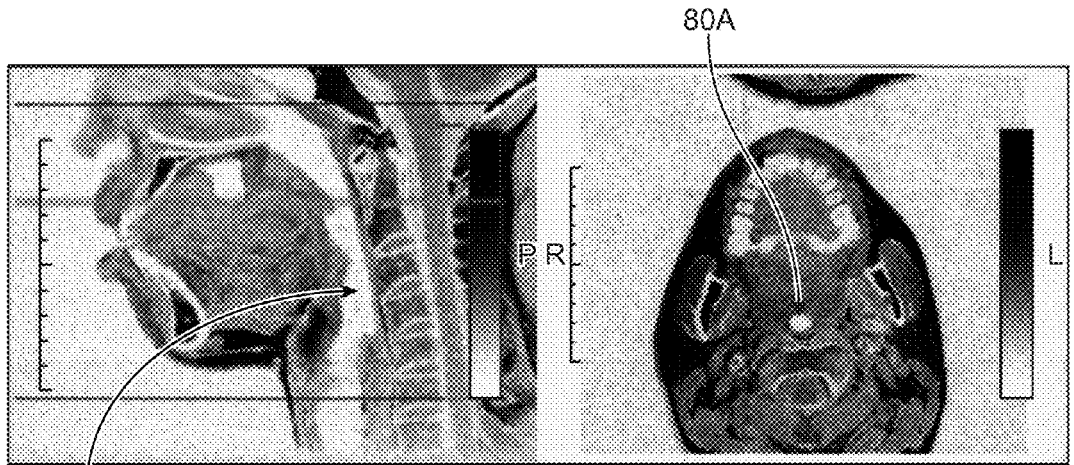
FIG. 8A1　　　　FIG. 8A2
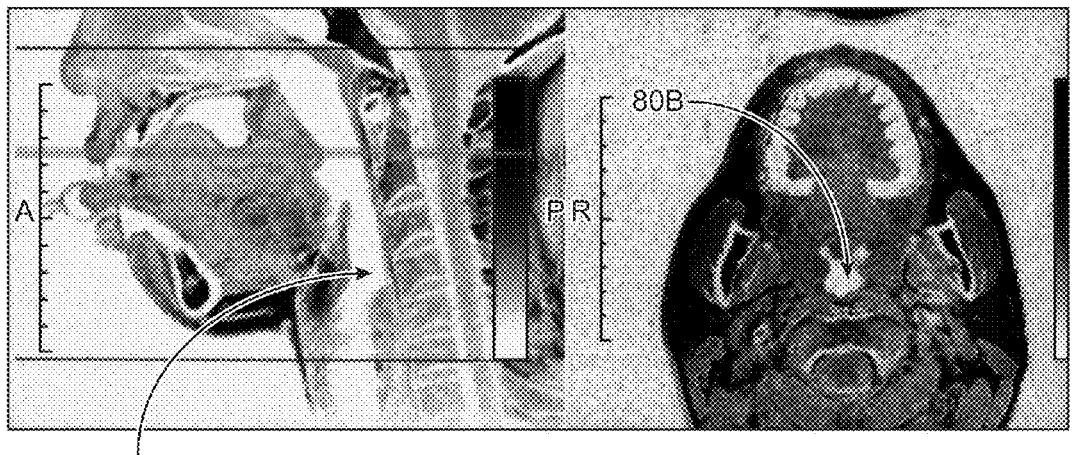
FIG. 8B1　　　　FIG. 8B2
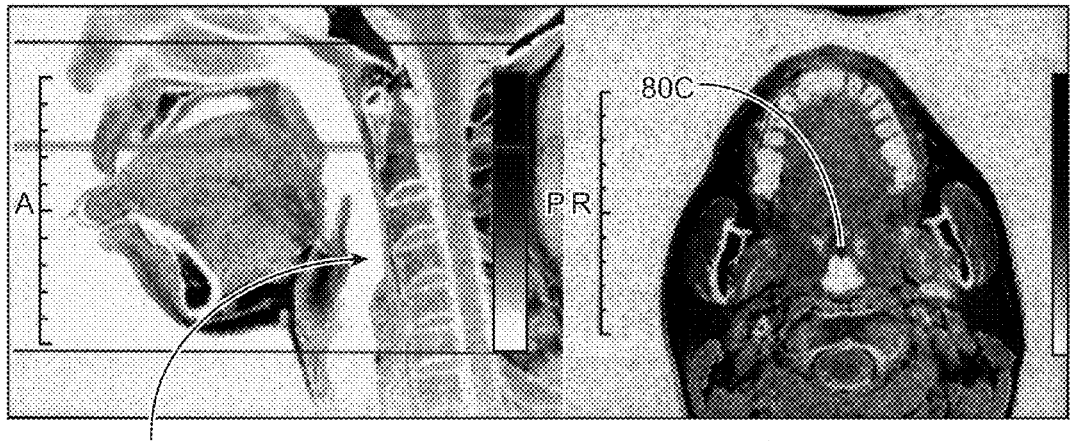
FIG. 8C1　　　　FIG. 8C2

ORAL DEVICE FOR ANTERIOR ADVANCEMENT OF THE TONGUE

CROSS-REFERENCE TO RELATED APPLICATION

This application is a continuation-in-part of U.S. patent application Ser. No. 13/759,793, filed Feb. 5, 2013, which is a continuation of U.S. patent application Ser. No. 13/593,137, filed Aug. 23, 2012, the entire contents of which are incorporated herein by reference.

BACKGROUND OF THE INVENTION

1. Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA. Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the forward end of the patient's mouth, typically at or just behind the lips, to pull the tongue forward in order to lift the rear portion of the tongue away from the back of the airway. See, for example, U.S. Pat. Nos. 6,494,209 and 7,328,698, and U.S. Patent Publication Nos. 2011/0259346; 2007/0277818; 2005/0166928 and 2005/0166929. While promising in theory, in practice it is very difficult to apply a vacuum in the region of the tip of the tongue to raise the base of the tongue and clear the patient's airway, particularly when the patient is lying on his or her back and gravity is pulling the tongue posteriorly. The tongue is a relatively large and compliant organ with significant mass, and applying a vacuum over a relatively small surface area at the tip will often not be effective in raising the back of the tongue against gravity. The moist and compliant tissues in the mouth are somewhat self-sealing, and this effect tends to inhibit the propagation of negative pressure, thereby confining the negative pressures to a relatively small area near the point of application. Thus, simply applying a vacuum at a location near the anterior tip of the tongue tends to draw the tongue up against the hard palate posterior to this location, creating a seal that restricts the propagation of vacuum through this region of contact toward the back of the oral cavity, where direct vacuum is usually required for maximum effectiveness.

As another improvement over CPAP, it has been proposed to place various devices in direct contact with the posterior tissues of the mouth such as the soft palate and posterior portions of the tongue. A major disadvantage of these approaches is that contact with certain tissues near the posterior area of the tongue may elicit the gag reflex and in any case the presence of such devices so far back in the mouth can be uncomfortable.

Still further improvements in the treatment of sleep apnea are described in U.S. Pat. Nos. 8,074,656; 8,074,656; and 8,122,889, and U.S. Patent Publication 2012/0017917, assigned to the assignee of the present application, the full disclosures of which are incorporated herein by reference. These patents describe engaging a lateral element across a medial region of the tongue to create a clearance above the tongue. By drawing a vacuum in the clearance, the soft palate can be drawn forward to open the airway. While very successful in many patients, the treatment is not fully effective in some patients.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. Moreover, the methods and devices should avoid contacting the portions of the oral cavity that trigger the gag reflex. The methods and systems should also be simple to implement and be effective to significantly improve patency of a patient's airway during sleep in a broad population of patients suffering from sleep apnea. At least some of these objectives will be met by the inventions described hereinafter.

2. Description of the Background Art

U.S. Pat. Nos. 8,074,656; 8,122,889; and 8,122,890, and U.S. Patent Publication Nos. 2012/007917 and 2012/0199135, assigned to the assignee of the present application, describe oral appliances for engaging a medial region of a patient's tongue to maintain airway patency. U.S. Pat. Nos. 6,595,209 and 7,328,698, and U.S. Patent Publication No. 2011/0259345, oral appliances for applying a vacuum to pull an anterior region of a patient's tongue forward to treat sleep apnea. See also Tsuiki et al. (2012) AM. J. Respir. Crit. Care Med. 185: A6461.

SUMMARY OF THE INVENTION

The present invention provides devices and methods for improving airway patency by simultaneously advancing an anterior region of a patient's tongue and constraining or depressing a medial region of the tongue while applying a first partial vacuum in a space created over the tongue by the constraint. In this way, both the tongue and the soft palate can be brought forward to clear the airway more reliably and for a greater number of patients than either action can consistently achieve by itself. In specific embodiments of the present invention, the tongue is brought forward by applying a second partial vacuum to an anterior region of the tongue, where the vacuum applied above the tongue and the vacuum applied to the anterior region of the tongue will usually be separately controlled and will usually be applied at different levels so that the patient and/or physician can separately adjust the levels of vacuum applied to the tongue and to the soft palate to optimize treatment for each individual patient.

In a first aspect of the present invention, an oral device is adapted for temporary placement in a patient's oral cavity. The oral device comprises a base, a tongue-engaging member, and a tongue pocket. The base is adapted to be held between the patient's upper and lower teeth, where the base has an anterior opening which is adapted to allow the patient's tongue to pass therethrough. The tongue-engaging member is coupled to the base, typically at a posterior end thereof, and is disposed to engage a medial region of the tongue when the base is positioned between the patient's teeth. The tongue pocket is usually coupled to the base and has an interior disposed to receive the anterior region of the patient's tongue when the tongue passes through the anterior opening in the base.

The tongue pocket is adapted to be connected directly or indirectly to a vacuum source to apply a partial vacuum within the pocket to draw the tongue forward when the tongue is present through the anterior opening. The tongue-engaging member of the oral device may also be connected to a vacuum source, and in some instances a single vacuum source may be used for both the tongue pocket and the tongue-engaging members. For example, the oral device may include passages and structure which allow a partial vacuum to be drawn in a region within the oral cavity disposed above the medial region of the tongue when the tongue-engaging member is engaged against the tongue. In such embodiments, the partial vacuum in the oral cavity may serve to draw the tongue into the tongue pocket. In other embodiments, as described in more detail below, the tongue pocket and tongue-engaging member each may have separate passages and structures for connection to separate vacuum sources for drawing vacuums within the tongue pocket and the patient's oral cavity, thus allowing different vacuum levels to be drawn in the pocket and in the oral cavity.

In specific embodiments of the devices of the present invention, the tongue/engaging member is adapted to be connected to a vacuum source to apply a partial vacuum in the oral cavity to draw the patient's soft palate toward a posterior surface of the tongue-engaging member. In other embodiments, a separate device or structure may be provided for drawing a vacuum in the region of the tongue-engaging member.

Both the tongue pocket and the tongue-engaging member will typically be provided with a single vacuum source, but alternatively they may be provided with separate vacuum sources which are separately connectable to the member and pocket, respectively. The vacuum sources will be separately controllable, and the vacuum source connected to or otherwise associated with the tongue-engaging member will typically be adapted to draw a vacuum in the range from 10 $cmH_2O$ to 75 $cmH_2O$, usually from 25 $cmH_2O$ to 50 $cmH_2O$. The partial vacuum applied by the tongue pocket will typically be higher (more negative), usually being in the range from 25 $cmH_2O$ to 100 $cmH_2O$, typically being in the range of 35 $cmH_2O$ to 55 $cmH_2O$. In further specific embodiments of the present invention, the tongue pocket will be provided with both a vacuum port for connecting to the vacuum source and a bleed port to allow a continuous flow and release of air through the tongue pocket while maintaining a partial vacuum. The resulting continuous flow through the tongue pocket, although often at a very low rate, will help draw moisture from the anterior of the tongue pocket and allow the connecting tubes and lines to be flushed to remove saliva which might otherwise collect.

The oral devices of the present invention will typically also include one or more vacuum sources which are connectable to the tongue pocket and to the tongue-engaging member. Typically, a first vacuum source is connectable to a vacuum port on the tongue pocket while the bleed port is attached to a flow regulator, such as a fixed orifice or variable control valve in order to help limit airflow through the tongue pocket and control the vacuum level within the pocket.

Similarly, a separate vacuum source may be connected to an outlet port of the tongue-engaging member with a flow regulator connected to the bleed port to allow fresh air to enter through the bleed port and to circulate before exiting to help clear moisture. As with the tongue pocket, the vacuum pump and/or the flow regulator will be controlled to maintain a target vacuum level within the oral cavity in the region of the tongue-engaging member. Usually, both vacuum pumps, both air flow regulators, and a programmable controller will be provided within a common housing which is connectable by a tube set to the oral device. In other cases, it might be possible to utilize a single vacuum source and/or a single flow regulator where the components would have at least two channels allowing for separate levels of vacuum to be applied to the tongue pocket and to the tongue-engaging member, respectively, or allow air flow to be separately regulated to each of the tongue pocket and the tissue-engaging member.

The pressures within the tongue pocket and in the region of the oral cavity near the tongue-engaging member will typically be controlled based on pressure and/or flow measurements of the air into and/or out of the tongue pocket and tissue-engaging member. The pressure will usually be controlled by conventional feedback control algorithms, and the vacuum pump will typically be a positive-displacement pump where the amount of air withdrawn (vacuum applied) can be adjusted by changing the speed of the pump. Such control systems are described in copending, commonly owned application Ser. No. 13/023,763, filed Feb. 9, 2011, the full disclosure of which is incorporated herein by reference.

In a second aspect of the present invention, methods for stabilizing a soft palate in patient's oral cavity comprise engaging a member against a medial region of the tongue to provide a clearance over the tongue. A vacuum is applied within the clearance to draw the soft palate toward a posterior region of the tongue. Simultaneously, an anterior region of the tongue is drawn forward in order to help clear the tongue and further open the patient's airway.

In specific embodiments, the anterior region of the tongue is drawn forward by capturing the tongue in a tongue pocket and applying a vacuum in the pocket. In preferred embodiments, the vacuum maintained in the clearance or region above the tongue and the vacuum maintained in the tongue pocket are controlled at different levels. Typically, the vacuum in the pocket will be in the range from 5 $cmH_2O$ to 150 $cmH_2O$, usually 35 $cmH_2O$ to 60 $cmH_2O$, while the pressure maintained in the region above the tongue is in the range from 25 $cmH_2O$ to 50 $cmH_2O$.

Both the vacuum in the tongue pocket and the vacuum in the clearance region over the tongue will be usually drawn simultaneously (at the same time) during at least a portion of the treatment cycle, where the vacuum in each is usually provided by drawing a vacuum with a positive displacement or other vacuum pump while simultaneously bleeding in a controlled amount of air while.

Embodiments of the present invention provide further devices and methods for improving airway patency by applying a first partial vacuum within the oral cavity through one or more ports oriented toward the teeth. The ports can be disposed on the upper surface of a U-shaped bite plate held between a patient's teeth. As the teeth are rigid, applying suction toward the teeth can reduce the risk of soft tissue occluding the ports. The upper surface of the bite plate is typically flat and the chewing surfaces of the teeth the ports are oriented toward are typically irregular. The ports can apply suction through the gaps or spaces between the upper surface of the bite plate and the chewing surfaces of the teeth. In this way, the airway can be cleared more reliably and more comfortably without the placement of structures on the medial and posterior regions of the tongue. In specific embodiments, the tongue is also brought forward by applying a second partial vacuum to an anterior region of the tongue. The vacuum applied within the oral cavity and the vacuum applied to the anterior region of the tongue will typically be a single, diffuse vacuum. In some embodiments, the vacuum applied within the oral cavity and the vacuum applied to the anterior region of the tongue is applied at different levels so that the patient and/or physician can separately adjust the levels of vacuum applied to the tongue and to the soft palate to optimize treatment for each individual patient.

This embodiment of the invention is advantageous as it can be made without any structure extending over the tongue. Some patients may find the tongue-bridging structure uncomfortable. In other patients, there is inadequate room in the oral cavity for the tongue-bridging structure. By drawing the vacuum through the teeth, pressure can be lowered throughout the oral cavity and within the tongue pocket to bring both the tongue and the soft palate forward to clear the airway.

An aspect of the present invention provides an oral device for temporary placement in a patient's oral cavity. The device comprises a base and optionally a tongue pocket. The base is adapted to be held between the patient's upper and lower teeth. The base defines an anterior opening which is adapted to allow the patient's tongue to pass therethrough. The base comprises one or more plates for receiving the patient's upper and lower teeth. The one or more plates have one or more tooth facing ports. The one or more tooth facing ports may be vertically oriented such that the one or more ports face the chewing surfaces of the nearby teeth when the base is held between the patient's upper and lower teeth. For example, the one or more ports may face the superior direction toward the lower surfaces of the upper teeth, e.g., the ports may be formed as apertures in the superior surface of the plates which contact the teeth. The tongue pocket is coupled to the base and has an interior disposed to receive an anterior region of the patient's tongue when the tongue passes through the anterior opening. The one or more ports are adapted to be connected to a vacuum source to apply a partial vacuum within the oral cavity (e.g., between a roof of the mouth and a medial region of the patient's tongue) such as when the tongue passes through the anterior opening of the base). The one or more ports may comprise a plurality of ports for applying a single diffuse, negative pressure in the posterior region of the oral cavity. Alternatively, different ports may apply a differential, negative pressure.

The one or more plates may comprise an upper plate for receiving the upper teeth and a lower plate for receiving the lower teeth. The upper and lower plates may diverge in the anterior direction so that the base holds the patient's upper teeth and lower teeth apart to provide the anterior opening therebetween. The upper and lower plates may each comprise a U-shaped bite plate configured to be positioned against full dentition. The base may further comprise a lip seal extending above the upper plate and below the lower plate to seal the patient's oral cavity when the base is held between the patient's teeth. The lip seal may comprise a peripheral portion and a core portion. The peripheral portion can be more flexible than the core portion so that the lip seal can spread out laterally as the patient or user bites down, which can allow the lip seal to better conform to the anatomy of the patient and provide improved comfort. The less flexible core portion can help to retain the shape of the lip seal so that the lip seal will not pop out of the patient's mouth as the patient bites down. The tongue pocket may extend in an anterior direction from the lip seal. The one or more tooth facing ports may be disposed only on the upper plate.

The tongue pocket is provided to accommodate the anterior end of the tongue which typically advances forward naturally as a partial vacuum is applied in the oral cavity. A vacuum or suction may not need to be applied to the tongue to cause such advancement, and in exemplary embodiments, the tongue pocket is simply a cavity which applies no suction or vacuum. In alternate embodiments, the tongue pocket may be adapted to be connected to a vacuum source to apply a partial vacuum in an interior of the tongue pocket to further draw the patient's tongue in an anterior direction. The oral device may further comprise a vacuum source which is connectable to one or more of the tooth facing port(s) of the base and optionally the tongue pocket. The vacuum source may comprise a single vacuum source which can be separately connected to and adjustable for each of the tooth facing port(s) and optionally the tongue pocket. The vacuum drawn through the ports of the base may be in a range from 10 cmH2O to 75 cmH2O. The vacuum drawn by the tongue pocket may be the same as the vacuum drawn through the ports of the base. For example, the vacuum drawn by the tongue pocket and through the ports of the base may comprise a single, diffuse vacuum. Alternatively, the partial vacuum applied by the tongue pocket may be higher than (more negative) the partial vacuum applied through the ports of the base, such as in the range of 25 cmH2O to 100 cmH2O. For example, the vacuum source can typically be adapted to draw a vacuum in the range from 35 cmH2O to 60 cmH2O in the tongue pocket and a vacuum in the range from 25 cmH2O to 50 cmH2O through the tooth facing port(s) of the base. In some embodiments, the vacuum source may comprise a plurality of vacuum sources, for example, one vacuum source for each of multiple vacuum channels in the oral device.

In some embodiments, one or more of the tongue pocket and the tooth facing port(s) of the base may each comprise a vacuum port and a bleed port to allow a continuous air flow while maintaining a partial vacuum. The oral device may further comprise a vacuum source connectable to one or more of the base and the tongue pocket. The vacuum source can be connectable to the vacuum and bleed ports of the tongue pocket and the vacuum and bleed ports of the base to provide a continuous air flow to each of the tooth facing port(s) of the base and the tongue pocket while maintaining a partial vacuum. Typically, a first vacuum source is connectable to a vacuum port on the tongue pocket while the bleed port is attached to a flow regulator, such as a fixed orifice or variable control valve in order to help limit airflow through the tongue pocket and control the vacuum level within the pocket. Similarly, a separate second vacuum source may be connected to an outlet port of the base with a flow regulator connected to the bleed port to allow fresh air to enter through the bleed port and to circulate before exiting to help clear moisture. As with the tongue pocket, the vacuum pump and/or the flow regulator will be controlled to maintain a target vacuum level within the oral cavity. Usually, both vacuum pumps, both air flow regulators, and a programmable controller will be provided within a common housing which is connectable by a tube set to the oral device. In other cases, it might be possible to utilize a single vacuum source and/or a single flow regulator where the components would have at least two channels allowing for separate levels of vacuum to be applied to the tongue pocket and to the tongue-engaging member, respectively, or allow air flow to be separately regulated to each of the tongue pocket and the tissue-engaging member.

In at least some instances, providing an air bleed within the oral cavity can cause a sensation of air flow across the tongue which may be uncomfortable for the user. In exemplary embodiments, no air bleed is provided within the oral cavity to avoid causing the air flow sensation. Alternatively, to regulate and measure air flow, an air bleed can be provided outside of the portion of the oral device that is placed in the patient's mouth. For example, an air bleed can be provided to the portion of the vacuum conduit connecting to the oral device.

The pressures within the tongue pocket and in the region of the oral cavity near base will typically be controlled based on pressure and/or flow measurements of the air into and/or out of the tongue pocket and the tooth facing ports of the base. The pressure will usually be controlled by conventional feedback control algorithms, and the vacuum pump will typically be a positive-displacement pump where the amount of air withdrawn (vacuum applied) can be adjusted by changing the speed of the pump. Such control systems are described in copending, commonly owned application Ser. No. 13/023,763, filed Feb. 9, 2011, the full disclosure of which is incorporated herein by reference.

Another aspect of the present invention provides a method for stabilizing a soft palate in a patient's oral cavity, which has a tongue and a palate. A tongue of the patient is passed through an anterior opening of a base held between the patient's upper and lower teeth. A vacuum is applied through one or more tooth facing ports of the base to draw together the soft palate and a posterior region of the tongue. The tooth facing port(s) may be disposed on one or more of an upper plate and a lower plate of the base. The tooth facing port(s) may be vertically oriented to face chewing surfaces of one or more of the patient's upper teeth and lower teeth when the base is held between the patient's upper teeth and lower teeth. For example, the tooth facing port(s) are oriented in the superior direction to face the lower surfaces of the upper teeth.

In exemplary embodiments, the vacuum applied through the tooth facing port(s) is a single, diffuse partial vacuum. Furthermore, an anterior region of the tongue may be drawn forward such as by capturing the tongue in a tongue pocket and optionally applying a vacuum in the pocket. In specific embodiments where a vacuum is also applied to the tongue pocket, the tongue pocket vacuum may be the same as the vacuum applied through the tooth facing port(s). In alternate embodiments, the vacuum applied through the tooth facing port(s) of the base may be at different levels than the vacuum applied to the tongue pocket. The vacuum applied through the tooth facing port(s) of the base may be less than the vacuum in the tongue pocket. For example, the vacuum applied through the one or more tooth facing ports of the base can be in the range from 25 cmH2O to 50 cmH2O and the vacuum in the tongue pocket can be in the range from 35 cmH2O to 60 cmH2O.

In alternative embodiments, the vacuum in the tongue pocket can be applied by continuously drawing a vacuum while simultaneously bleeding in a controlled amount of air to maintain a desired partial vacuum. The vacuum through the tooth facing port(s) of the base can be applied by continuously drawing a vacuum while simultaneously bleeding in a controlled amount of air to maintain a desired partial vacuum. In at least some instances, providing an air bleed can cause a sensation of air flow across the tongue which may be uncomfortable for the user. In exemplary embodiments, no air bleed is provided within the oral cavity to avoid causing the air flow sensation. To regulate and measure air flow, an air bleed may be provided outside of the portion of the oral device that is placed in the patient's mouth. For example, an air bleed can be provided to the portion of the vacuum conduit connecting to the oral device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 7A, 7B, 7C1, and 7C2 are schematic illustrations of control systems or consoles suitable for use with the oral devices of the present invention for applying partial vacuums in the oral cavity of a test subject through one or more ports of the oral device base.

FIGS. 8A1 and 8A2 are sagittal and transverse cross-sections, respectively, of a test subject's upper airway, the patient wearing an oral appliance for engaging a medial region of a patient's tongue to maintain airway patency.

FIGS. 8B1 and 8B2 are sagittal and transverse cross-sections, respectively, of a test subject's upper airway, the patient wearing an oral appliance for engaging a medial region of a patient's tongue to maintain airway patency which also has a tongue pocket.

FIGS. 8C1 and 8C2 are sagittal and transverse cross-sections, respectively, of a test subject's upper airway, the patient wearing an oral appliance having a tongue pocket and one or more tooth oriented vacuum ports.

DETAILED DESCRIPTION OF THE INVENTION

Figure 1:
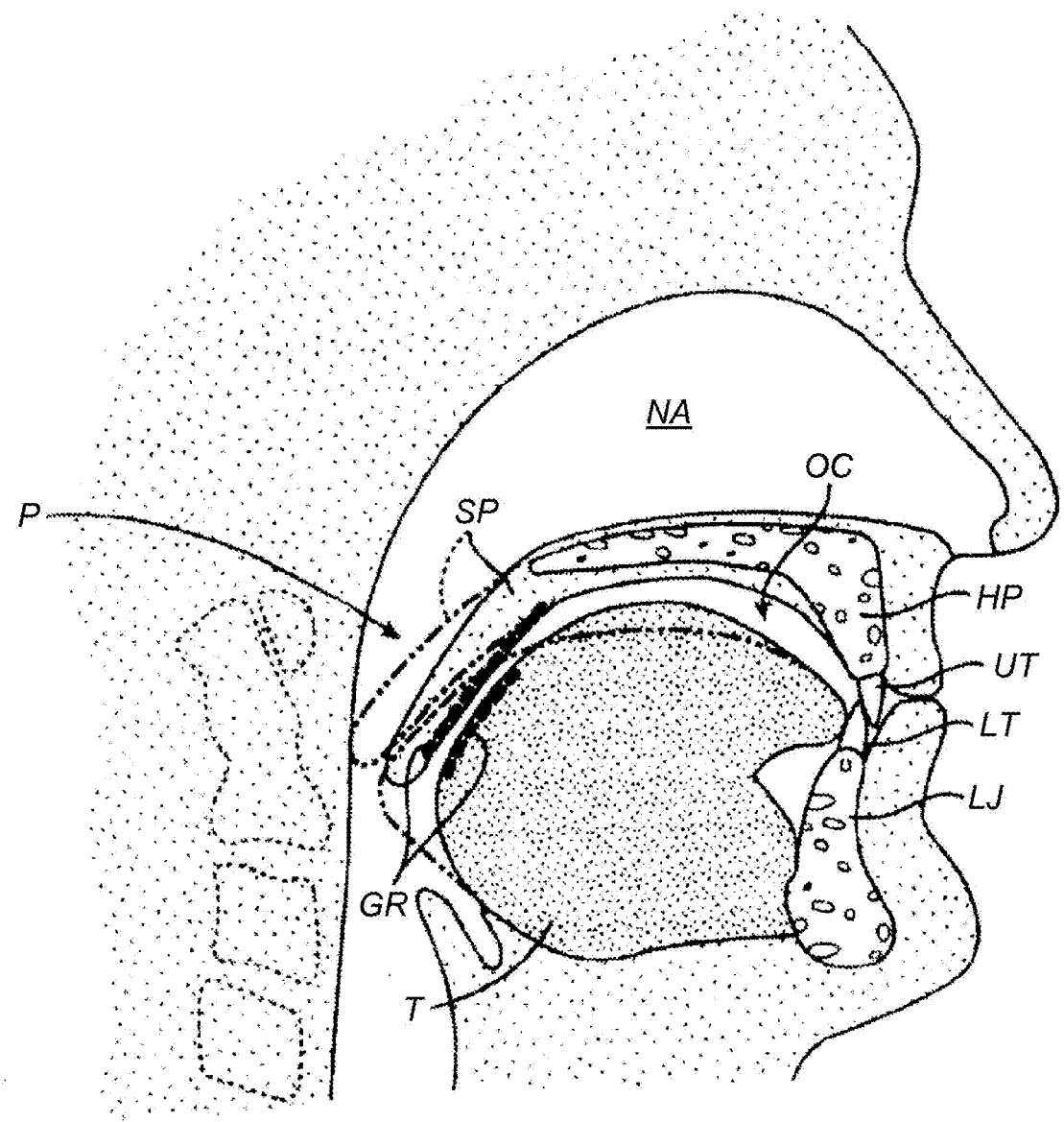
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

As used herein, "superior" refers to the direction toward the top of the oral cavity (or top of the head), "inferior" refers to the direction opposite the superior direction, "anterior" refers to the direction toward the front of the oral cavity or lips, and "posterior" refers to the direction toward the back of the oral cavity and airway, opposite the anterior direction. The terms "patency" and "airway" refer to the opening or clearing of the airway leading from the nasal cavity into the trachea located generally behind the soft palate and the rear of the tongue. To improve airway patency, the airway may be wholly or partially obstructed intermittently or temporarily for some time period over a normal sleep cycle, however, the airway will be open or partially open more than it would in the patient's untreated condition. The "upper portion of the soft palate" refers to the superior portion of the soft palate extending inferiorly from the end which connects to the hard palate to a point about ⅓-½ way toward the free inferior tip of the soft palate. The phrase "medial region" or "medial surface" of the tongue refers to a superior surface of the tongue which is spaced substantially posteriorly from the anterior tip of the patient's tongue and immediately anterior or forward of the region which initiates the gag reflex. While it may vary from patient to patient, the medial region will generally be the middle one third of the upper surface of the tongue which extends between the anterior tip of the tongue and the posterior end of the tongue (the posterior end being the location on the tongue that is furthest posterior in the oral cavity); i.e., the medial surface will usually include an area of the tongue that is at least about ⅓ of the way, more preferably at least about ½ of the way, from the anterior tip of the tongue to the posterior end of the tongue. Preferably, the medial region will include an area on the tongue posterior to the midpoint between the anterior and posterior ends of the hard palate. The phrase "clear region" refers to the space or volume above and/or posterior of the tongue which will be cleared by the methods and devices of the present invention. The clearing will usually be achieved by engaging a surface which is inclined forwardly relative to a plane of the base when the base is positioned between the upper and lower teeth and against the superior surface of the tongue, typically using a member or element which engages the tongue and which is anchored within the oral cavity so as to simultaneously advance the tongue in an anterior direction and depress the tongue in an inferior direction to open or maintain the clear region and allow the negative pressure to draw the soft palate against the tongue. The term "vacuum" and the phrase "negative pressure" each refers to a total or partial vacuum which is maintained in the clear region, typically by controlled aspiration, where the pressure is maintained primarily in the range from 5 cmH$_2$O to 150 cmH$_2$O below the local atmospheric pressure. The "occlusal plane" is the plane in which the upper and lower teeth meet when the patient bites the upper and lower teeth together.

Figure 2A:
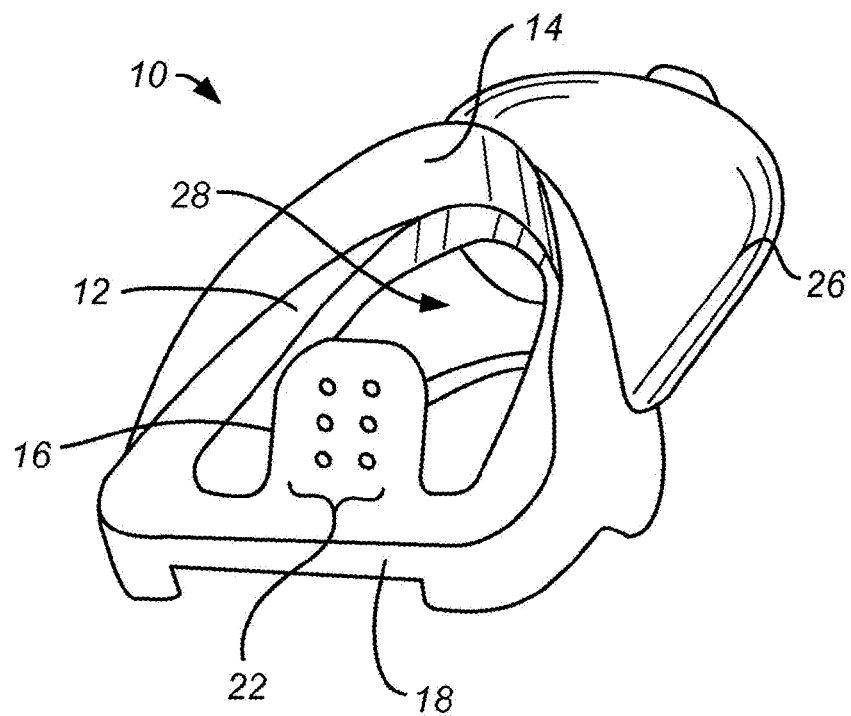
FIGS. 2A and 2B illustrate an embodiment of an oral device constructed in accordance with the principles of the present invention with FIG. 2A providing a posterior to anterior perspective and FIG. 2B showing an anterior to posterior perspective.
Figure 2B:
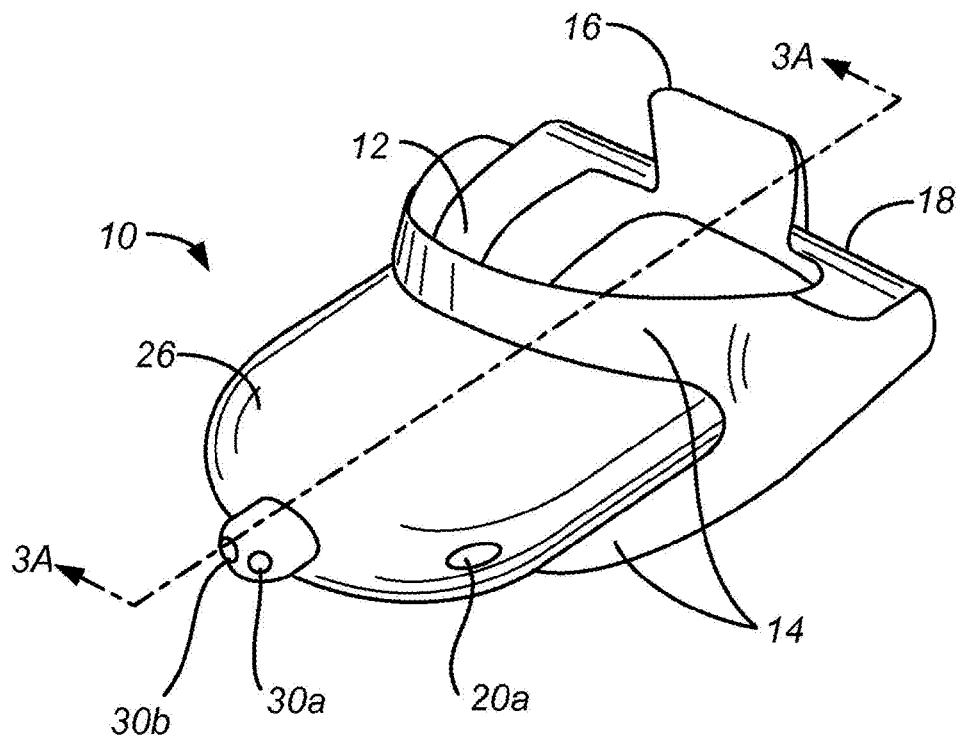

Referring now to FIGS. 2A and 2B an exemplary oral device 10 constructed in accordance with the principles of the present invention comprises a U-shaped base or anchor structure 12 having a lip seal 14 at its forward or anterior end. A tongue-engaging member 16 extends upwardly from a lateral support 18 which extends between the posterior ends of the base 12. Ports 20a and 20b (shown in FIG. 4) are provided for drawing a vacuum within the lateral support 18 which in turn can draw a partial vacuum within the patient's oral cavity through a plurality of vacuum ports 22 on a posterior surface of the tongue-engaging member 16. As described thus far, the oral device 10 is very similar to the device described in commonly owned Patent Publication No. 2012/0017917, the full disclosure of which incorporated herein by reference.

Figure 3A:
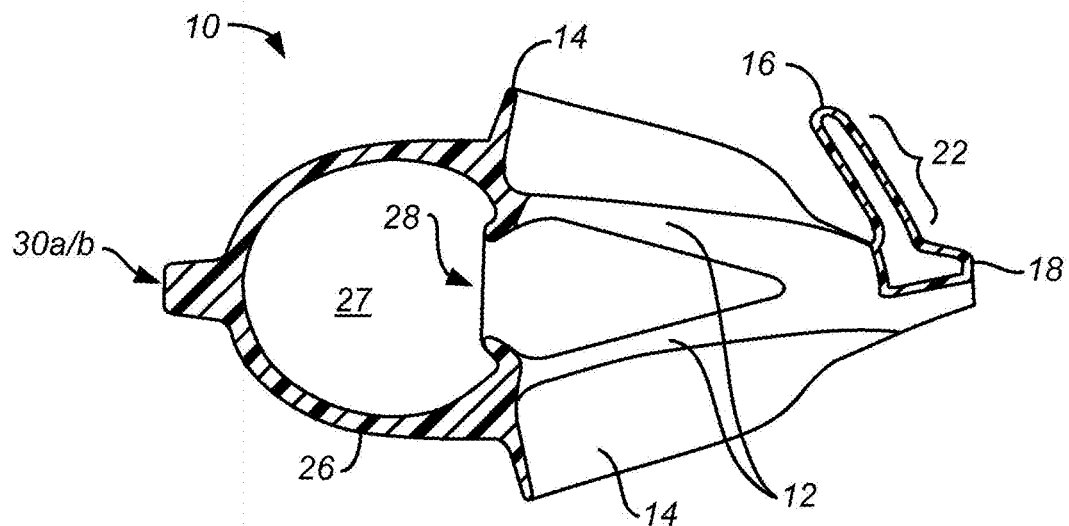
FIG. 3A is a cross-sectional view of the embodiment of FIGS. 2A and 2B taken along line 3A-3A shown in FIG. 2B.
Figure 3B:
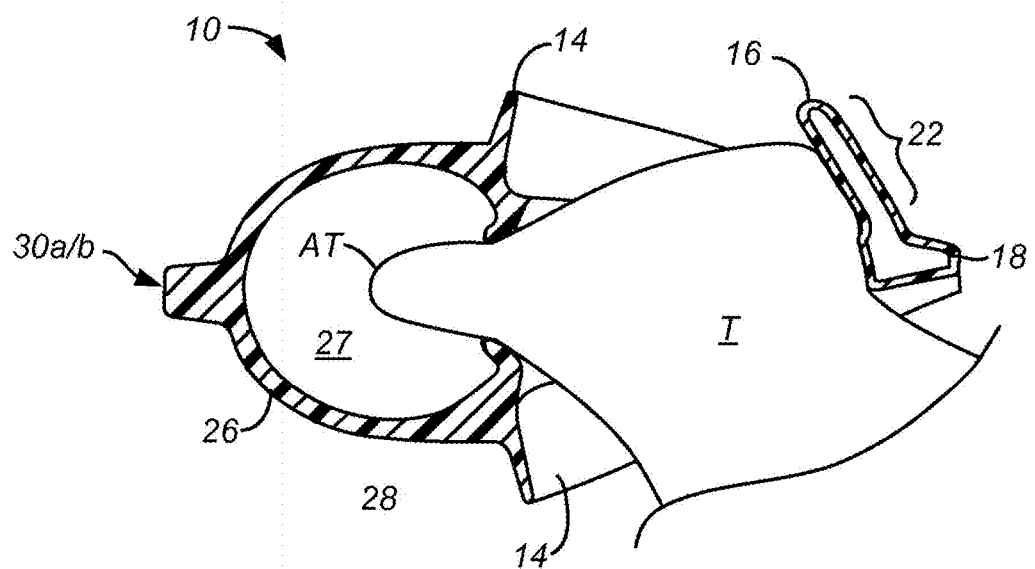
FIG. 3B is a cross-sectional view of the embodiment similar to FIG. 3A shown with a tongue being drawn into an anterior pocket and being engaged by a tongue-engaging member.

The oral devices of the present invention will further include a structural component for drawing an anterior end of the tongue forward in order to enhance clearing of the patient's airway. As shown in FIGS. 3A and 3B, the structure for advancing the tongue may comprise a dome or "tongue pocket" 26 which is secured to a forward or anterior end of the base 12 and lip seal 14. The tongue pocket 26 defines an open, interior space 27 in which a vacuum is drawn which can pull the anterior tip AT of a patient's tongue T forward through an anterior opening 28, as seen in FIG. 3B. The vacuum may be drawn through ports 30a and 30b, as described in more detail below.

Figure 4:
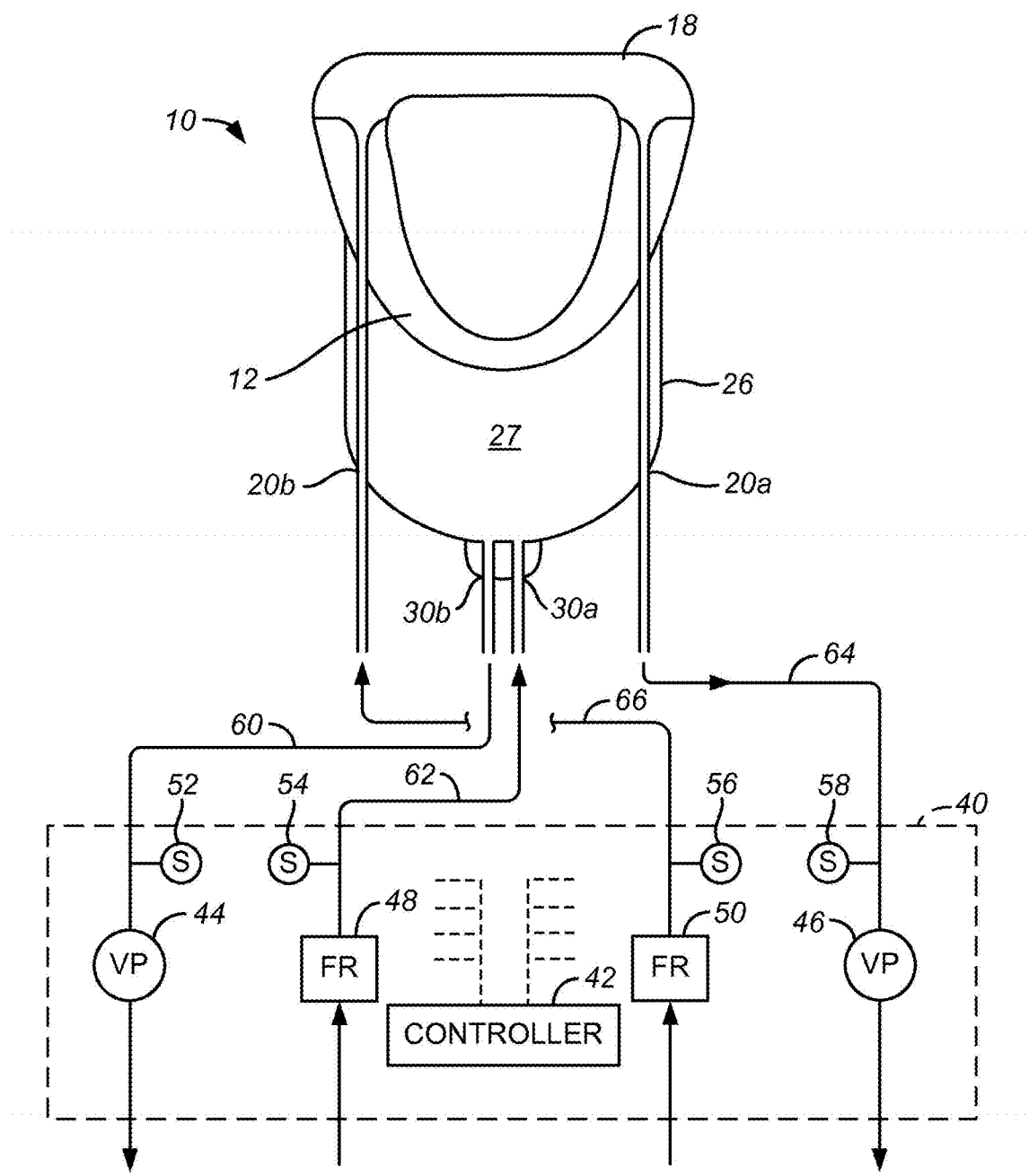
FIG. 4 is a schematic illustration of a control system or console suitable for use with the oral devices of the present invention for independently maintaining partial vacuums in the tongue pocket and in a region surrounding the tongue-engaging member.

Referring now to FIG. 4, partial vacuums may be selectively applied to the lateral support 18 and the interior 27 of the tongue pocket 26 using a console or tabletop control unit 40. The console 40 will typically include a controller 42 which will usually include a microprocessor and a dedicated interface (not shown). Conventional inputs and readouts (not illustrated) will be provided on the console 40 so that a patient or a physician can monitor operation of the system and adjust system parameters such as turning the system off and on, separately controlling and adjusting the partial vacuums drawn in the lateral support 18 (which in turn draws the vacuum in the medial and posterior regions of the patient's oral cavity) and in the interior 27 of the tongue cavity 26.

The partial vacuum in the interior 27 of the tongue pocket 26 is drawn by a vacuum pump 44 which is attached to port 30b by a tubular connector 60. The vacuum pump 44 is typically a positive displacement pump, such as a diaphragm pump, and the volume of air removed from the interior 27 can be controlled by controlling the speed of the vacuum pump 44 which in turn will control the level of vacuum within the interior, as discussed above. Typically, an air bleed is allowed to flow into the interior 27 through a second tubular connection 62, where the flow rate is controlled by a flow restrictor 48 such as a fixed orifice, a variable flow control or pressure control valve, or the like. The vacuum level in the interior 27 of the tongue pocket 26 may be controlled, for example, by monitoring the pressure and/or flow rates of the air leaving and entering through the tubular connectors 60 and 62 using sensors 52 and 54. Typically, the pressures will be monitored and the speed of the vacuum pump 44 will be adjusted to achieve the desired vacuum level.

Similarly, the level of vacuum within the lateral support 18 (which determines the vacuum within the patient's oral cavity), will be maintained by a vacuum pump 46 which is connected to port 20a by a tubular connector 64. An air bleed stream will typically be provided through a tubular connector 66 which is connected through port 20b, where the air bleed is restricted by flow restrictor 50, which can be a fixed orifice and adjustable valve, or the like. Pressures and/or volume flow rates are monitored by sensors 56 and 58, and the controller 42 can collect the pressure and/or flow rate data in order to control the level of vacuum within the lateral support 18.

Figure 5A:
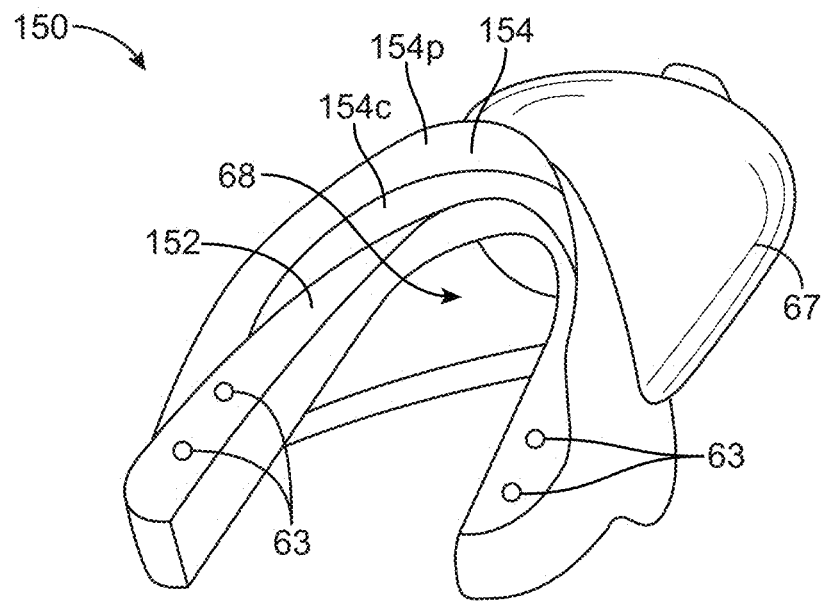
FIGS. 5A and 5B illustrate another embodiment of an oral device constructed in accordance with the principles of the present invention with FIG. 5A providing a posterior to anterior perspective and FIG. 5B showing an anterior to posterior perspective.
Figure 5B:
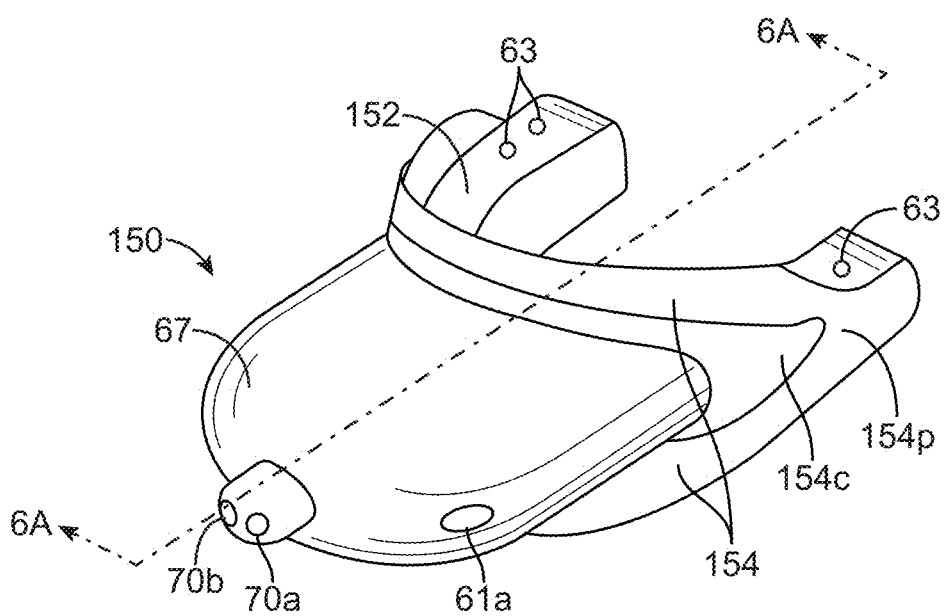

Referring now to FIGS. 5A and 5B, an exemplary oral device 150 constructed in accordance with the principles of the present invention is shown. The oral device 150 comprises a U-shaped base or anchor structure 152 having a lip seal 154 at its forward or anterior end. The lip seal 154 may be constructed of a soft, flexible biocompatible material such as a thermoplastic elastomer or TPE (e.g., GLS CL30). The lip seal 154 may comprise a peripheral portion 154p and a core portion 154c. The peripheral portion 154p will typically be flexible to allow the lip seal 154 to spread out laterally when a user bites down on the oral device 150. Often, the peripheral portion 154p will be more flexible than the core portion 154c. The more rigid core portion 154c can help to retain the shape of the lip seal 152 so that the lip seal 152 will not pop out of the patient's mouth as the patient bites down. The core portion 154c may comprise a flexible plastic, may be molded into the lip seal 154, or may comprise malleable mesh, wires, or foils constructed of materials such as stainless steel, titanium, or NiTi. By being flexible and malleable, the lip seal 154 can fit better with the anatomy of the patient or user and provide improved comfort.

Ports 70a and 70b are provided for drawing a vacuum within the U-shaped base or anchor structure 152. This vacuum can in turn draw a partial vacuum within the patient's oral cavity through a plurality of tooth-facing, vertically oriented ports 63 or a superior or upper surface of the U-shaped base or anchor structure 152. Alternatively or in combination, ports 61a and 61b (shown in FIG. 7A) can be provided for drawing a vacuum within the U-shaped base or anchor structure 152 which in turn can draw a partial vacuum within the patient's oral cavity OC through the vertically oriented ports 63.

In exemplary embodiments, the one or more vertically oriented ports 63 are provided on a superior or upper surface of the U-shaped base or anchor structure 152. The one or more vertically oriented ports 63 may instead be provided on an inferior or lower surface of the U-shaped base or anchor structure 152 or on both the inferior and superior surfaces.

Figure 6A:
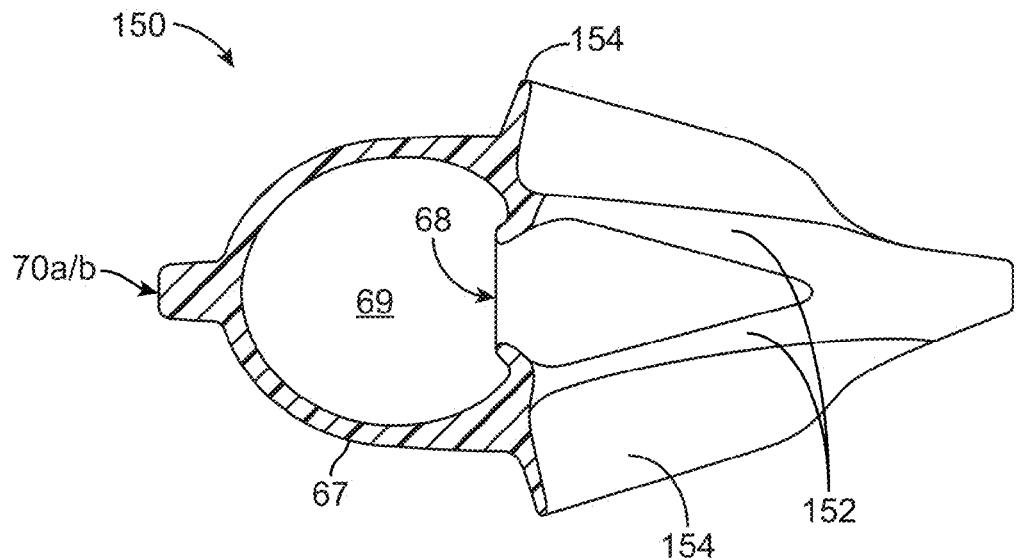
FIG. 6A is a cross-sectional view of the embodiment of FIGS. 5A and 5B taken along line 6A-6A shown in FIG. 5B.
Figure 6B:
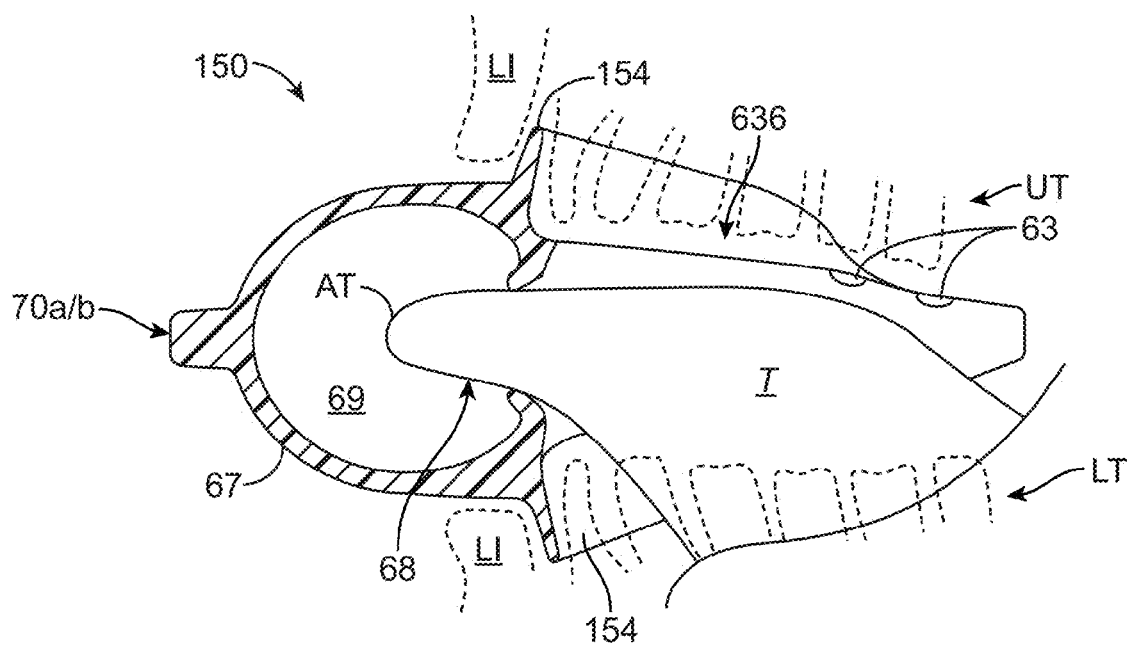
FIG. 6B is a cross-sectional view of the embodiment of FIG. 6A shown with the tongue being drawn into an anterior pocket and the teeth engaging a bite plate.

The oral device 150 will further include a structural component for accommodating the forward advancement of an anterior end of the tongue in order to enhance clearing of the patient's airway. As shown in FIGS. 6A and 6B, the structure for advancing the tongue may comprise a dome or "tongue pocket" 67 which is secured to a forward or anterior end of the base 152 and lip seal 154. As shown in FIGS. 5A and 5B, the lip seal core portion 154c is disposed between the tongue pocket 67 and the lip seal peripheral portion 154p. The lips LI of the test subject or patient are shown in FIG. 6B in broken line over the lip seal 154. The tongue pocket 67 defines an open, interior space 69. In exemplary embodiments, no vacuum is drawn in the tongue pocket 67 and the anterior tip AT of the tongue is left to advance naturally through an anterior opening 68 into the tongue pocket 67 as a partial vacuum is drawn in the oral cavity with the ports 63. Alternatively, a second vacuum can be drawn in the tongue pocket 67 which can pull the anterior tip AT of a patient's tongue T forward through the anterior opening 68. The vacuum may be drawn through ports 70a and 70b, which may lead to ports 71c and 71d (FIG. 7B) open to the tongue pocket 67 as described in more detail below.

FIG. 6B also shows the upper teeth UT and lower teeth LT of the test subject or patient in broken line as biting down on the U-shaped base or anchor structure 152, which can act as a bite plate. The ports 63 face superiorly toward the lower surface of the upper teeth UT. A vacuum can be drawn through ports 63. As the teeth are rigid, applying suction toward the teeth can reduce the risk of soft tissue occluding the ports 63. The upper surface of the U-shaped base or anchor structure 152 is typically flat and the lower chewing surfaces of the upper teeth UT are typically irregular. Thus, there are gaps or spaces 63G between the upper surface of the U-shaped base or anchor structure 152 and the lower chewing surfaces of the upper teeth UT. The partial vacuum is applied through these gaps or spaces 63G. In this way, the airway can be cleared more reliably and more comfortably without the placement of structures on the medial and posterior regions of the tongue.

Alternatively or in combination, the ports 63 may be oriented in other directions toward the teeth to apply the partial vacuum through gaps between the planar surfaces of the bite structure and the teeth. For example, the ports 63 may be provided on the U-shaped base or anchor structure 152 to face inferiorly toward the upper surface of the lower teeth LT. In another example, the U-shaped base or anchor structure 152 may further comprise a U-shaped side wall facing the inner or outer lateral sides of the teeth (or both), and the ports 63 may be provided thereon to apply the partial vacuum between the gaps defined by the U-shaped side wall and the inner or outer lateral sides of the teeth.

Figure 7A:
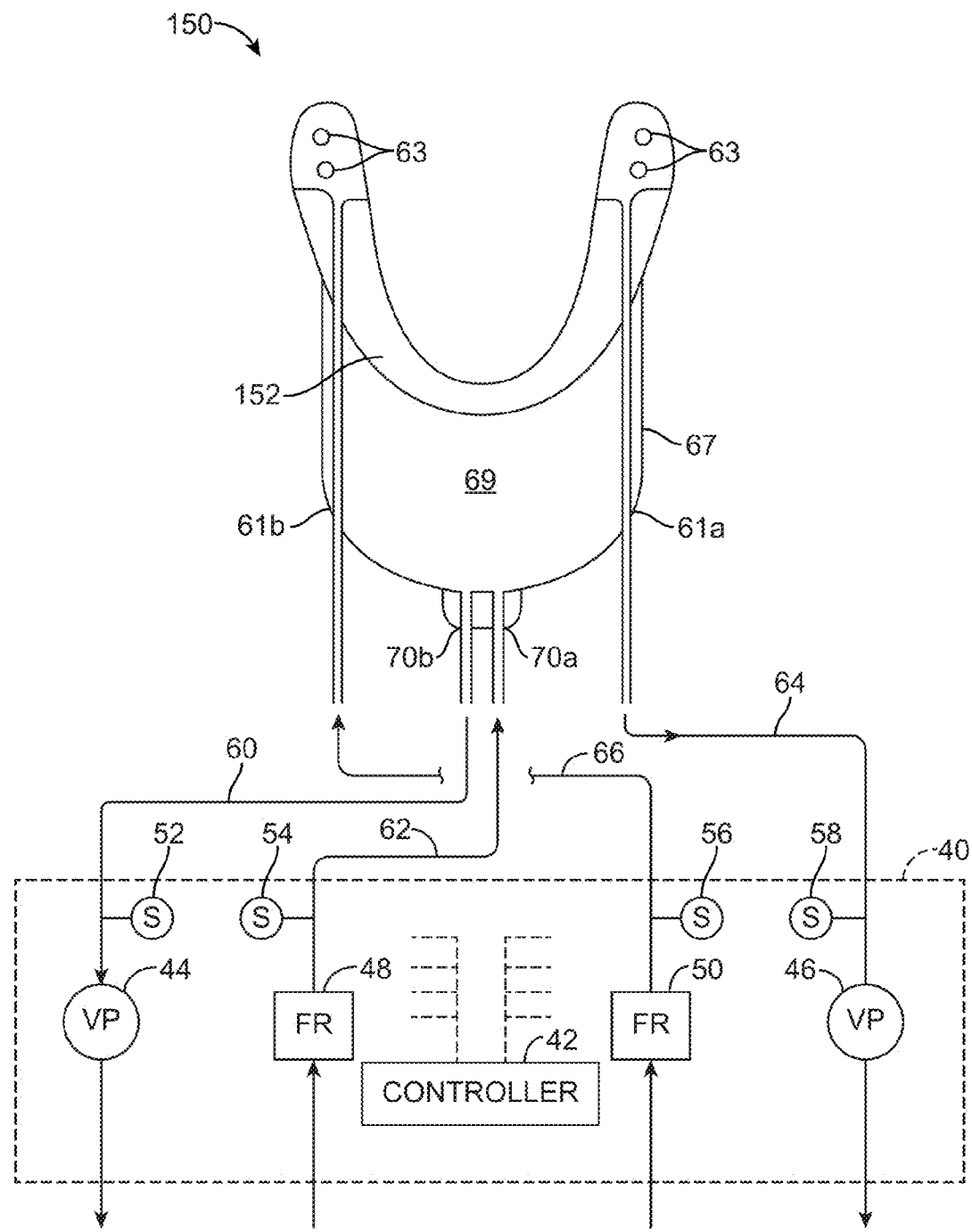

Referring now to FIG. 7A, partial vacuums may be selectively applied to the U-shaped base or anchor structure 152 and the interior 69 of the tongue pocket 67 using a console or tabletop control unit 40. The console 40 will typically include a controller 42 which will usually include a microprocessor and a dedicated interface (not shown). Conventional inputs and readouts (not illustrated) will be provided on the console 40 so that a patient or a physician can monitor operation of the system and adjust system parameters such as turning the system off and on, separately controlling and adjusting the partial vacuums drawn in the U-shaped base or anchor structure 152 (which in turn draws the vacuum in the medial and posterior regions of the patient's oral cavity through the gaps 63G between the planar upper surface of the U-shaped base or anchor structure 152 and the irregular chewing surfaces of the upper teeth UT) and in the interior 69 of the tongue cavity 67.

The partial vacuum in the interior 69 of the tongue pocket 67 can be drawn by a vacuum pump 44 which is attached to port 70b by a tubular connector 60. The vacuum pump 44 may also couple to conduit 61b to draw a partial vacuum through ports 63. The vacuum pump 44 is typically a positive displacement pump, such as a diaphragm pump, and the volume of air removed from the interior 69 can be controlled by controlling the speed of the vacuum pump 44 which in turn will control the level of vacuum within the interior, as discussed above. An air bleed can be allowed to flow into the interior 69 through a second tubular connection 61a, where the flow rate is controlled by a flow restrictor 48 such as a fixed orifice, a variable flow control or pressure control valve, or the like. The vacuum level in the interior 69 of the tongue pocket 67 may be controlled, for example, by monitoring the pressure and/or flow rates of the air leaving and entering through the tubular connectors 60 and 62 using sensors 52 and 54. Typically, the pressures will be monitored and the speed of the vacuum pump 44 will be adjusted to achieve the desired vacuum level.

Similarly, the level of vacuum within the U-shaped base or anchor structure 152 (which determines the vacuum within the patient's oral cavity), will be maintained by a vacuum pump 46 which is connected to port 61a by a tubular connector 64. An air bleed stream can be provided through a tubular connector 66 which is connected through port 61b, where the air bleed is restricted by flow restrictor 50, which can be a fixed orifice and adjustable valve, or the like. Pressures and/or volume flow rates are monitored by sensors 56 and 58, and the controller 42 can collect the pressure and/or flow rate data in order to control the level of vacuum within the U-shaped base or anchor structure 152.

In at least some cases, providing an air bleed to flow into the oral cavity at the same time a partial vacuum is drawn can cause a sensation of airflow across the patient's tongue which may be uncomfortable for the patient. In exemplary embodiments, a partial vacuum is drawn in the oral cavity without providing an air bleed to flow into the oral cavity. For example, an air bleed may simply not be provided at all, as described below with reference to FIG. 7B, or air bleed may be provided outside of the portion of the oral device that is placed within the patient's mouth, as described below with reference to FIGS. 7C1 and 7C2.

Figure 7B:
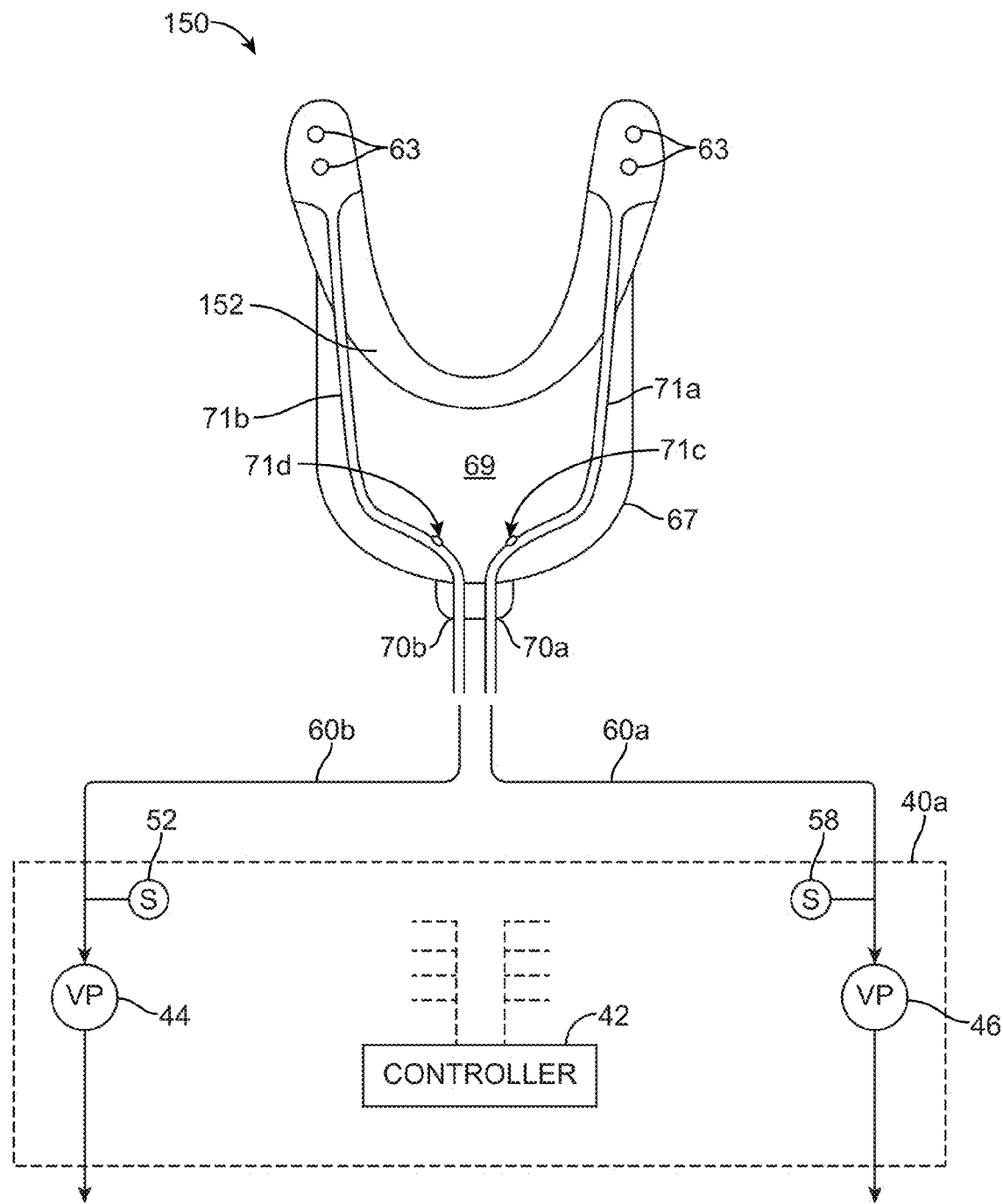

Referring now to FIG. 7B, a partial vacuum may be applied to the U-shaped base or anchor structure 152 and optionally the interior 69 of the tongue pocket 67 using a console or tabletop control unit 40a. The console or tabletop control unit 40a may be similar in many respects to console or tabletop control unit 40 described above. The vacuum pump 44 is coupled to port 70b of the oral device 150 through a conduit 60b, and the vacuum pump 46 is coupled to port 70a of the oral device 150 through conduit 60a. The ports 63 on a first side of the U-shaped base or anchor structure 152 are coupled to the port 70b through a conduit 71b within the oral device 150, and the ports 63 on the other second side of the U-shaped base or anchor structure 152 are coupled to the port 70a through a conduit 71a within the oral device 150. While FIG. 7B shows two vacuum pumps 44 and 46, a single vacuum pump coupled to both conduits 60a and 60b may instead be used to apply a single, diffuse partial vacuum through the ports 63, for example as shown in FIGS. 7C1 and 7C2.

The ports 63 on the first side of the U-shaped base or anchor structure 152, the conduit 71b, the port 70b, and the conduit 60b can form a first vacuum pathway. The ports 63 on the second side of the U-shaped base or anchor structure 152, the conduit 71a, the port 70a, and the conduit 60a can form a second vacuum pathway. The components of the vacuum pathways will typically have a sufficient inner diameter to minimize clogging due to saliva bubbles. For example, the components of the vacuum pathways may have an inner diameter of at least 3/32 inches. Where the inner diameters of the vacuum pathways are insufficiently wide, one of the two vacuum pathways may become clogged with saliva bubbles while the other performs the primary vacuum function until that pathway itself becomes clogged. The subsequent clogging can then cause the first pathway to clear and perform the primary vacuum function instead. The resulting flip flopping can create uncomfortable oral sensations for the patient or user.

In some embodiments, ports 71c and 71d open to the interior 69 of the tongue pocket 67 can be provided so that a partial vacuum can be drawn in the tongue pocket 67. As shown in FIG. 7B, the port 71c may be coupled to the port 70a, and the port 71d may be coupled to the port 70b. The vacuum level in the oral cavity OC and in the interior 69 of the tongue pocket 67 where applicable may be controlled, for example, by monitoring the pressure and/or flow rates of the air flowing through the tubular connectors 60a and 60b using sensors 52 and 58, respectively. Typically, the pressures will be monitored and the speed of the vacuum pumps 44 and 46 will be adjusted to achieve the desired vacuum level. In many embodiments, a single, diffuse partial vacuum is provided through the ports 63 and the tongue pocket 67.

FIG. 7C1 shows a schematic illustration of another control system or console suitable for use with the oral device 150. A partial vacuum may be applied to the U-shaped base or anchor structure 152 and optionally the interior 69 of the tongue pocket 67 using a console or tabletop control unit 40b. The console or tabletop control unit 40b may be similar in many respects to console or tabletop control unit 40a described above. A single vacuum pump 44 is coupled to ports 70a and 70b of the oral device 150 through a conduit 60b. An air bleed stream can be provided through the flow restrictor 48 and the conduit 60a which couples to the port 70a. FIG. 7C2 shows a magnified schematic view of the ports 70a and 70b. As shown in FIG. 7C2, the ports 70a and 70b comprise two elongate channels or conduits coupled together through a middle channel or conduit. The middle channel or conduit separates the ports 70a and 70b into an anterior portion leading to the vacuum pump 44 and a posterior portion leading to the conduits 71a and 71b, respectively, of the oral device 150. Air from the oral cavity is drawn through a first air flow pathway 72a from port 70a leading to the conduit 71a and through a second air flow pathway 72b from port 70b leading to the conduit 71b. The air flow pathways 72a and 72b combine into an air flow pathway 72 which is drawn by the vacuum pump 44. The air bleed is flows through pathway 74 within the ports 70a and 70b. The air bleed can then flow through the flow regulator 48, which may comprise a fixed orifice or variable control valve, in order to help limit airflow into the ports 70a and 70b.

In the embodiment shown by FIG. 7C1, the ports 63 on the first side of the U-shaped base or anchor structure 152, the conduit 71b, the port 70b, and the conduit 60b can form a first vacuum pathway, and the ports 63 on the second side of the U-shaped base or anchor structure 152, the conduit 71a, the port 70a, and the conduit 60b can form a second vacuum pathway. The components of the vacuum pathways will typically have a sufficient inner diameter to minimize clogging due to saliva bubbles. For example, the components of the vacuum pathways may have an inner diameter of at least 3/32 inches. Where the inner diameters of the vacuum pathways are insufficiently wide, one of the two vacuum pathways may become clogged with saliva bubbles while the other performs the primary vacuum function until that pathway itself becomes clogged. The subsequent clogging can then cause the first pathway to clear and perform the primary vacuum function instead. The resulting flip flopping can create uncomfortable oral sensations for the patient or user.

In some embodiments, ports 71c and 71d open to the interior 69 of the tongue pocket 67 can be provided so that a partial vacuum can be drawn in the tongue pocket 67. As shown in FIG. 7C1, the port 71c may be coupled to the port 70a, and the port 71d may be coupled to the port 70b. The vacuum level in the oral cavity OC and optionally in the interior 69 of the tongue pocket 67 where applicable may be controlled, for example, by monitoring the pressure and/or flow rates of the air flowing through the tubular connectors 60a and 60b using sensors 52 and 54, respectively. Typically, the pressures will be monitored and the speed of the vacuum pump 44 and the flow restrictor 48 will be adjusted to achieve the desired vacuum level. In many embodiments, a single, diffuse partial vacuum is provided through the ports 63 and the tongue pocket 67.

Experimental Section.

The inventors have tested various oral appliances for the treatment of sleep apnea and other conditions to analyze their affect on the test subject's upper airway. Images of the test subject's upper airway with the various oral appliances worn were taken as shown in FIGS. 8A1-8C2. In FIGS. 8A1-8C2, the reference letter A refers to the anterior direction, the reference letter P refers to the posterior direction, the reference letter R refers to the direction to the right, and the reference letter L refers to the direction to the left.

A first oral appliance having a lateral element placed across a medial region of the tongue to create a clearance above the tongue was tested. By drawing a vacuum in the clearance, the soft palate can be drawn forward to open the airway. FIG. 8A1 shows a sagittal cross-sectional image of the test subject's upper airway with the first oral appliance. FIG. 8A2 shows a transverse cross-section of the same.

A second oral appliance according to embodiments of the present invention was tested. For example, the second oral appliance may comprise exemplary oral device 10. The second oral appliance has a lateral element placed across a medial region of the tongue to create a clearance above the tongue as well as a tongue pocket for accommodating the tongue in the anterior direction was tested. By drawing a vacuum in the clearance, the soft palate can be drawn forward to open the airway. In at least some instances, drawing a vacuum above the tongue can cause the tongue to advance in the anterior direction such that providing a tongue pocket to accommodate the anterior region of the tongue would be helpful. Additionally, a vacuum can be drawn in the anterior direction to further drawn the tongue into the tongue pocket. FIG. 8B1 shows a sagittal cross-sectional image of the test subject's upper airway with the second oral appliance. FIG. 8B2 shows a transverse cross-section of the same. As shown in FIGS. 8B1 and 8B2, the airway 80B provided by the second oral appliance is wider than the airway 80A provided by the first oral appliance.

A third oral appliance according to embodiments of the present invention was tested. For example, the third oral appliance may comprise exemplary oral device 50. The third oral appliance has a bite plate with one or more tooth facing vacuum ports. By drawing a vacuum through these ports, a vacuum can be drawn through the gaps or spaces between the planar bite surfaces of the bite plate and the irregular chewing surfaces of the teeth to draw a partial vacuum above the tongue, drawing forward the soft palate. In at least some instances, drawing a vacuum above the tongue can cause the tongue to advance in the anterior direction such that providing a tongue pocket would be helpful. Additionally, a further partial vacuum can be drawn in the anterior direction to further draw the tongue into the tongue pocket. FIG. 8C1 shows a sagittal cross-sectional image of the test subject's upper airway with the third oral appliance. FIG. 8C2 shows a transverse cross-section of the same. As shown in FIGS. 8C1 and 8C2, the airway 80C provided by the third oral appliance is wider than the airway 80A provided by the first oral appliance and comparable to the airway 80B provided by the second oral appliance. In at least some instances, the lack of a lateral element placed across the medial region of the tongue can provide an additional degree of comfort for the test subject or patient. In at least some instances, due to a lack of space within the test subject's or patient's oral cavity, such as in pediatric patients, the third oral appliance which lacks a lateral element to be placed across the medial region of the tongue may be preferred over the second oral appliance which has such a lateral element.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral device for temporary placement in a patient's oral cavity, said device comprising:
    a base adapted to be held between the patient's upper and lower teeth,
    wherein the base comprises one or more plates for receiving the patient's upper and lower teeth, the one or more plates comprising upper and lower bite surfaces configured to contact chewing surfaces of the patient's upper and lower teeth when the base is held therebetween,
    wherein one or more of the upper or lower bite surfaces of the one or more plates have one or more tooth facing ports adapted to be connected to a vacuum source to apply a partial vacuum within the oral cavity when the base is held between the patient's upper and lower teeth, and
    wherein the one or more tooth facing ports are vertically oriented toward the chewing surfaces of one or more of the patient's upper or lower teeth to direct the vacuum such that risk of soft tissue occluding the one or more tooth facing ports is reduced.

2. An oral device as in claim 1, wherein the one or more plates comprise an upper plate for receiving the upper teeth and a lower plate for receiving the lower teeth, wherein the upper and lower plates are configured to hold the upper's teeth and lower teeth apart to provide an anterior opening therebetween, and wherein the upper plate comprises the upper bite surface and the lower plate comprises the lower bite surface.

3. An oral device as in claim 2, wherein the base further comprises a lip seal extending above the upper plate and below the lower plate to seal the patient's oral cavity when the base is held between the patient's teeth.

4. An oral device as in claim 3, further comprising a tongue pocket coupled to the base and having an interior disposed to receive an anterior region of the patient's tongue when the tongue passes through the anterior opening, wherein the tongue pocket extends in an anterior direction from the lip seal.

5. An oral device as in claim 3, wherein the lip seal comprises a flexible core.

6. An oral device as in claim 2, wherein the upper and lower plates each comprise a U-shaped bite plate configured to be positioned against a full dentition.

7. An oral device as in claim 2, wherein the one or more tooth facing ports are disposed only on the upper plate to face and direct the vacuum toward a chewing surface of the patient's upper teeth.

8. An oral device as in claim 1, further comprising a tongue pocket coupled to the base and having an interior disposed to receive an anterior region of the patient's tongue when the tongue passes through an anterior opening of the base, the anterior opening being adapted to allow the patient's tongue to pass therethrough.

9. An oral device as in claim 8, wherein the tongue pocket is adapted to be connected to a vacuum source to apply a partial vacuum in an interior of the tongue pocket to draw the patient's tongue in an anterior direction.

10. An oral device as in claim 9, further comprising a vacuum source which is connectable to one or more of the base or the tongue pocket.

11. An oral device as in claim 10, wherein the vacuum source comprises a single vacuum source and wherein the single vacuum source is separately connected to the base and the tongue pocket through at least two channels which are adjustable for each of the base and the tongue pocket.

12. An oral device as in claim 10, wherein the vacuum source is adapted to draw a vacuum in the tongue pocket and a vacuum through a tongue-engaging member, the vacuum in the tongue pocket and the vacuum through the tongue-engaging member being at same levels.

13. An oral device as in claim 10, wherein the vacuum source is adapted to draw a vacuum in the tongue pocket and a vacuum through a tongue-engaging member, the vacuum in the tongue pocket and the vacuum through the tongue-engaging member being at different levels.

14. An oral device as in claim 1, wherein the one or more tooth facing ports are vertically oriented to face and direct the vacuum toward the chewing surface of one or more of the patient's upper or lower teeth.

15. An oral device as in claim 1, wherein the partial vacuum is applied between a roof of the mouth and a medial region of the patient's tongue.

16. An oral device for temporary placement in a patient's oral cavity, said device comprising:
a base adapted to be held between the patient's upper and lower teeth,
wherein the base comprises one or more plates for receiving the patient's upper and lower teeth,
wherein the one or more plates have one or more tooth facing ports adapted to be connected to a vacuum source to apply a partial vacuum within the oral cavity when the base is held between the patient's upper and lower teeth,
wherein the one or more tooth facing ports are located at a medial or posterior portion of the patient's dentition when the base is held between the patient's upper and lower teeth, and
wherein the one or more tooth facing ports are vertically oriented toward chewing surfaces of one or more of the patient's upper or lower teeth to direct the vacuum at a medial or posterior portion of the patient's oral cavity.

17. An oral device as in claim 16, wherein the one or more plates comprise an upper plate for receiving the upper teeth and a lower plate for receiving the lower teeth, wherein the upper and lower plates are configured to hold the upper's teeth and lower teeth apart to provide an anterior opening therebetween.

18. An oral device as in claim 17, wherein the base further comprises a lip seal extending above the upper plate and below the lower plate to seal the patient's oral cavity when the base is held between the patient's teeth.

19. An oral device as in claim 18, further comprising a tongue pocket coupled to the base and having an interior disposed to receive an anterior region of the patient's tongue when the tongue passes through the anterior opening, wherein the tongue pocket extends in an anterior direction from the lip seal.

20. An oral device as in claim 18, wherein the lip seal comprises a flexible core.

21. An oral device as in claim 17, wherein the upper and lower plates each comprise a U-shaped bite plate configured to be positioned against a full dentition.

22. An oral device as in claim 17, wherein the one or more tooth facing ports are disposed only on the upper plate to face and direct the vacuum toward a chewing surface of the patient's upper teeth.

23. An oral device as in claim 16, further comprising a tongue pocket coupled to the base and having an interior disposed to receive an anterior region of the patient's tongue when the tongue passes through an anterior opening of the base, the anterior opening being adapted to allow the patient's tongue to pass therethrough.

24. An oral device as in claim 23, wherein the tongue pocket is adapted to be connected to a vacuum source to apply a partial vacuum in an interior of the tongue pocket to draw the patient's tongue in an anterior direction.

25. An oral device as in claim 24, further comprising a vacuum source which is connectable to one or more of the base or the tongue pocket.

26. An oral device as in claim 25, wherein the vacuum source comprises a single vacuum source and wherein the single vacuum source is separately connected to the base and the tongue pocket through at least two channels which are adjustable for each of the base and the tongue pocket.

27. An oral device as in claim 25, wherein the vacuum source is adapted to draw a vacuum in the tongue pocket and a vacuum through a tongue-engaging member, the vacuum in the tongue pocket and the vacuum through the tongue-engaging member being at same levels.

28. An oral device as in claim 25, wherein the vacuum source is adapted to draw a vacuum in the tongue pocket and a vacuum through a tongue-engaging member, the vacuum in the tongue pocket and the vacuum through the tongue-engaging member being at different levels.

29. An oral device as in claim 16, wherein the one or more tooth facing ports are vertically oriented to face and direct the vacuum toward the chewing surface of one or more of the patient's upper or lower teeth.

30. A method for stabilizing a soft palate in a patient's oral cavity, the patient's oral cavity having a tongue and a palate, said method comprising:
providing a base to be held between the patient's upper and lower teeth; and
applying a vacuum through one or more tooth facing ports of the base to draw together the soft palate and a posterior region of the tongue,
wherein the one or more tooth facing ports are vertically oriented toward chewing surfaces of one or more of the upper or lower teeth to direct the vacuum such that risk of soft tissue occluding the one or more tooth facing ports is reduced when the base is held between the patient's upper and lower teeth.

31. A method as in claim 30, further comprising drawing an anterior region of the tongue forward.

32. A method as in claim 31, wherein drawing the anterior region of the tongue forward further comprises capturing the tongue in a tongue pocket through an anterior opening of the base.

33. A method as in claim 32, further comprising applying a vacuum in the tongue pocket.

34. A method as in claim 33, wherein the vacuum applied through the one or more tooth facing ports of the base and the vacuum in the tongue pocket are maintained at different levels.

35. A method as in claim 34, wherein the vacuum applied through the one or more tooth facing ports of the base is less than the vacuum in the tongue pocket.

36. An oral device as in claim 35, wherein the partial vacuum is applied between a roof of the mouth and a medial region of the patient's tongue.

37. A method as in claim 33, wherein the vacuum applied through the one or more tooth facing ports of the base and the vacuum in the tongue pocket are maintained at same levels.

38. A method as in claim 30, wherein the one or more tooth facing ports are disposed on one or more of an upper plate or a lower plate of the base.

39. A method for stabilizing a soft palate in a patient's oral cavity, the patient's oral cavity having a tongue and a palate, said method comprising:
providing a base to be held between the patient's upper and lower teeth; and
applying a vacuum through one or more tooth facing ports of the base to draw together the soft palate and a posterior region of the tongue,
wherein the one or more tooth facing ports are located at a medial or posterior portion of the patient's dentition when the base is held between the patient's upper and lower teeth, and
wherein the one or more tooth facing ports are vertically oriented toward chewing surfaces of one or more of the patient's upper or lower teeth so that the vacuum is applied at a medial or posterior portion of the patient's oral cavity.

40. A method as in claim 39, further comprising drawing an anterior region of the tongue forward.

41. A method as in claim 40, wherein drawing the anterior region of the tongue forward further comprises capturing the tongue in a tongue pocket through an anterior opening of the base.

42. A method as in claim 41, further comprising applying a vacuum in the tongue pocket.

43. A method as in claim 42, wherein the vacuum applied through the one or more tooth facing ports of the base and the vacuum in the tongue pocket are maintained at different levels.

44. A method as in claim 43, wherein the vacuum applied through the one or more tooth facing ports of the base is less than the vacuum in the tongue pocket.

45. A method as in claim 42, wherein the vacuum applied through the one or more tooth facing ports of the base or the vacuum in the tongue pocket are maintained at same levels.

46. A method as in claim 39, wherein the one or more tooth facing ports are disposed on one or more of an upper plate or a lower plate of the base.

* * * * *